United States Patent [19]

Mund et al.

[11] Patent Number: 4,853,091

[45] Date of Patent: Aug. 1, 1989

[54] METHOD AND APPARATUS FOR THE ELECTROCHEMICAL DETERMINATION OF OXYGEN CONCENTRATION

[75] Inventors: Konrad Mund, Uttenreuth; Walter Preidel, Erlangen; J. Raghavendra Rao; Gerhard Richter, both of Erlangen, all of Fed. Rep. of Germany

[73] Assignee: Siemens Aktiengesellschaft, Berlin and Munich, Fed. Rep. of Germany

[21] Appl. No.: 186,755

[22] Filed: Apr. 26, 1988

Related U.S. Application Data

[63] Continuation of Ser. No. 763,464, Aug. 7, 1985.

[30] Foreign Application Priority Data

Aug. 10, 1984 [DE] Fed. Rep. of Germany ....... 3429583

[51] Int. Cl.$^4$ ............................................. G01N 27/46
[52] U.S. Cl. ..................................... 204/1 T; 204/402; 204/403; 204/412; 204/431; 128/637; 128/639; 128/642
[58] Field of Search ............... 204/1 T, 1 Y, 1 P, 415, 204/402, 431, 432, 412, 403; 128/637, 639, 642

[56] References Cited

U.S. PATENT DOCUMENTS

| | | | |
|---|---|---|---|
| 2,414,411 | 1/1947 | Marks | 204/1 Y |
| 2,913,386 | 11/1959 | Clark | 204/415 |
| 3,259,124 | 7/1966 | Hillier et al. | 204/415 |
| 3,260,656 | 7/1966 | Ross | 204/415 |
| 4,076,596 | 2/1978 | Connery et al. | 204/415 |
| 4,166,775 | 9/1979 | Bruckenstein | 204/415 |
| 4,419,210 | 12/1983 | Wang | 204/415 |
| 4,496,454 | 1/1985 | Berger | 204/402 |
| 4,505,784 | 3/1985 | Mund et al. | 204/402 |

FOREIGN PATENT DOCUMENTS

| | | |
|---|---|---|
| 8301687 | 5/1983 | PCT Int'l Appl. . |
| 1531761 | 11/1978 | United Kingdom ............ 204/402 |
| 2019580 | 10/1979 | United Kingdom . |
| 2059597 | 4/1981 | United Kingdom . |

OTHER PUBLICATIONS

*Medical and Biological Applications of Electrochemical Devices,* "Polarographic Determination of Oxygen in Biological Materials", Kreuzer, Kimmich, and Brezina, 1980, Chapter 6, pp. 174–217.

*Primary Examiner*—T. Tung
*Attorney, Agent, or Firm*—Kenyon & Kenyon

[57] ABSTRACT

The electrochemical determination of the oxygen concentration, particularly in biological matter, is possible by means of an oxygen sensor with a measuring electrode and a counter electrode over long periods of time, even if the sensor is implanted, by taking the following measures; two potentials are cyclically impressed on the measuring electrode, with one potential (measuring potential) in the range $-1.4\text{ V} \leq pAg/AgCl \leq -0.4\text{ V}$, and the other potential (recovery potential) in the range $-0.2\text{ V} \leq pAg/AgCl \leq +0.2\text{ V}$; the dwelling time at the measuring potential is small as compared to the duration of the cycle; and the current flowing during the measuring period is evaluated as the measuring signal.

15 Claims, 4 Drawing Sheets

METHOD AND APPARATUS FOR THE ELECTROCHEMICAL DETERMINATION OF OXYGEN CONCENTRATION

This application is a continuation, of application Ser. No. 763,464, filed Aug. 7, 1985.

BACKGROUND OF THE INVENTION

This invention relates to a method and apparatus for the electrochemical determination of the oxygen concentration, particularly in biological matter, by means of an oxygen sensor with a measuring electrode and a counterelectrode.

In modern medicine, implantable heart pacemakers are used increasingly for the therapy of heart arrythmia. The heart muscle is stimulated by short current pulses which are transmitted by means of a stimulating electrode. The implantable heart pacemakers generally operate with a constant frequency and thus only imperfectly simulate the control of the healthy heart which changes its beat as required. Therefore, physiological control of the rate or frequency of heart pacemakers is desired, for which purpose, for instance, the oxygen concentration in the blood or tissue can be used as a control parameter. The frequency of the stimulating pulses is then adapted to the oxygen concentration or the partial oxygen pressure in order to make the heart beat faster if the oxygen supply is insufficient. For this purpose, the oxygen concentration must be measured continuously, i.e., an implantable oxygen sensor is required. Besides their use in heart pacemakers, oxygen sensors are also suitable for determining the oxygen content in respiration and can therefore be used in anesthetics and intensive patient monitoring.

Heretofore the oxygen concentration in the blood or tissue has been measured generally extracorporally but only to a very limited extent and only for a short time in vivo. As the basis for the measurement, the electrochemical principle, for which purpose a so-called Clark cell is employed has essentially been used heretofore (see U.S. Pat. Nos. 2,913,386; 3,260,656 and 4,076,496). In such an oxygen sensor, a diaphragm is arranged in front of the measuring electrode, whereby a diffusion limiting current adjusts itself at the electrode, i.e., a measuring signal proportional to the concentration is obtained.

The above-mentioned measuring methodology is not suited for long-term implantation since the limiting current depends heavily on the diffusion layer. Thus, the connective tissue layer, which is of necessity formed in the body after the implantation, can therefore falsify the measuring signal. In principle, the solution of this problem consists of using diaphrams which can be implanted over the long term. Diaphragms suited for this purpose, however, are not yet known to date.

It is an object of the invention to describe a method and apparatus which allows the determination of the oxygen concentration over long periods of time even if the sensor is implanted, using an oxygen sensor with a measuring and counterelectrode.

SUMMARY OF THE INVENTION

According to the present invention, this object is achieved by cyclically impressing two potentials on the measuring electrode, where the one potential (the measuring potential) is in the range $-1.4\ V \leq \rho Ag/AgCl \leq -0.4\ V$ and the other potential (the recovery potential) is in the range $-0.2\ V \leq \rho Ag/AgCl \leq +0.2\ V$; by making the dwelling time for the measuring potential small as compared to the duration of the cycle; and by evaluating the current flowing during the measuring period as the measuring signal.

The present invention doe not require the use of a diaphragm and thereby avoids the disadvantages connected therewith. The basic principle of this method and apparatus consists of the provision that during the measurement as little oxygen as possible is taken from the immediate environment of the measuring electrode, for instance, from the tissue, so that this environment is not appreciably oxygen-depleted. In this manner the tissue does not degenerate, i.e., it is not converted into connective tissue but remains intact. Such an oxygen sensor is therefore particularly well suited for long term implantation, i.e., for a period of several years.

In practice, the principle underlying the present invention is realized in such a manner that initially, for a relatively long time, a potential is impressed on the measuring or sensor electrode, at which no oxygen reaction and no electrode corrosion takes place, namely, the so-called recovery potential. Then, a measuring potential is impressed on the electrode in such a manner that the oxygen reaction takes place to such a degree as is required for the measurement, but the oxygen consumption remains as low as possible. This is achieved by a relatively short dwelling time at the measuring potential, i.e., by a duration of the measuring potential which is small as compared to the duration of the cycle or the recovery phase. The recovery phase is relatively long so that the oxygen loss occurring during the measurement is compensated by replenishment from the tissue.

The duration of the cycle, i.e. the cycle time, in the method according to the present invention is advantageously betwen 0.5 and 10 seconds and preferably between 1 and 5 seconds. The dwelling time at the measuring potential is advantageously between 5 and 100 msec and preferably between 10 and 50 msec. The dwelling time at the measuring potential is preferably smaller by at least a factor 20 than the cycle duration.

In the method according to the present invention, which proceeds without disturbing and without adversely affecting the surroundings of the electrode, the reduction current which depends on the oxygen concentration is determined and evaluated as the measuring signal. Advantageously, the current flowing during the measuring period is integrated and the charge integral is evaluated as the measuring signal.

The evaluation of the current or its integration takes advantageously place with some time delay, i.e., with a time delay relative to the start of the measuring period. In this manner, the charge reversal of the electrode double-layer capacity which occurs in the first 2 to 5 msec, is eliminated in the evaluation, i.e., only the reaction current itself is considered. Advantageously, the current is evaluated 2 to 40 msec and preferably 10 to 15 msec after the start of the measuring period.

The measuring electrode of the oxygen sensor used in the present invention is preferably a smooth vitreous carbon electrode. Vitreous carbon which has already found acceptance as the material for the stimulating electrode of heart pacemakers (see, for instance, DE-OS 26 13 072) is body compatible and is surrounded in the body by connective tissue with a thickness of less than 100 μm. Such a connective tissue layer does not impede the diffusion of oxygen to the surface of the measuring electrode. Since vitreous carbon does not have much catalytic activity, substances contained in the body are, moreover, hardly absorbed and therefore trigger no reactions. Besides vitreous carbon, gold and pyrographite, for instance, can be used as the material for the measuring or sensor electrode. Electrode materials of the kind mentioned are otherwise known per se (see in this connection: F. Kreuzer, H.P. Kimmich, and M. Brezina in J. Koryta "Medical and Biological Applications of Electrochemical Devices", John Wiley & Sons, Ltd., 1980, page 173ff).

The counter electrode consists of a material which is inert as well as biocompatible and has a high double layer capacity relative to the measuring electrode. Preferably, the counter electrode is a platinum electrode. As further electrode materials can be used, for instance, activated vitreous carbon, i.e., vitreous carbon with a microporous surface layer (see in this connection DE-OS 26 13 072) and titanium nitride (DE-OS 33 00 668).

Besides the measuring and the counter electrode, the oxygen sensor used in the method according to the present invention may further comprise a reference electrode. An Ag/AgCl electrode is preferably used as the reference electrode. Such an electrode can be produced, for instance, by anodizing a silver wire in a solution containing chloride or by immersion of a silver wire into a silver chloride melt.

The oxygen sensor itself then consists of two or three electrode arrangement, the electrodes advantageously being joined together in the form of a small catheter probe. In this manner the electrode arrangement can easily be inserted into the blood, for instance, through veins or into the tissue.

The method according to the invention can be used in oxygen sensors for controlling heart pacemakers as well as in other medical applications, particularly in anesthetics and patient monitoring. In addition, this principle is also suitable in environment analysis and for process control.

DETAILED DESCRIPTION

A preferred embodiment of the oxygen sensor employed with the present invention comprises the following electrodes:

A measuring electrode of smooth, i.e., not activated, vitreous carbon, a platinum sheet forming the counter electrode and an Ag/AgCl reference electrode (electrolyte: 3 m KCl). In the experimental samples of the oxygen sensor, these electrodes are arranged in a cell of glass. In tests the operation was in part with a rotating measuring electrode (200 RPM), in the form of a cylindrical rod (diameter: 2 mm; cylinder surface: 0.19 cm$^2$). In disc shaped measuring electrodes which likewise have a diameter of 2 mm, the area is 0.03 cm$^2$.

In a 3 electrode arrangement of the type mentioned above, the measuring electrode can also consist of gold, i.e., a gold rod may be used. In an oxygen sensor with a 2 electrode arrangement, for instance, a smooth vitreous carbon electrode used as the measuring electrode may be combined with a large area disc of activated vitreous carbon (diameter: 4 cm) as the counter electrode.

With oxygen sensors of the type mentioned above, clearly reproducible measuring signals are obtained which depend on the oxygen concentration, and thereby also have good calibration curves, even if different electrolytes are used. For instance, a physiological salt solution (with 0.9 percent NaCl and 0.1 percent NaHCO$_3$) was used as an electrolyte; about 150 ml of this solution were used in each case (base electrolyte). The base electrolyte may also contain physiological substances such as glucose, urea and amino acids. For preparing such an electrolyte, 1 g/l glucose, 388 mg/l urea and 398.3 mg/l of an amino acid mixture (of 16 amino acids, always in the physiologically maximal concentration) are added to the base electrolyte. Cow serum or human serum was also used as the electrolyte.

Figure 1:
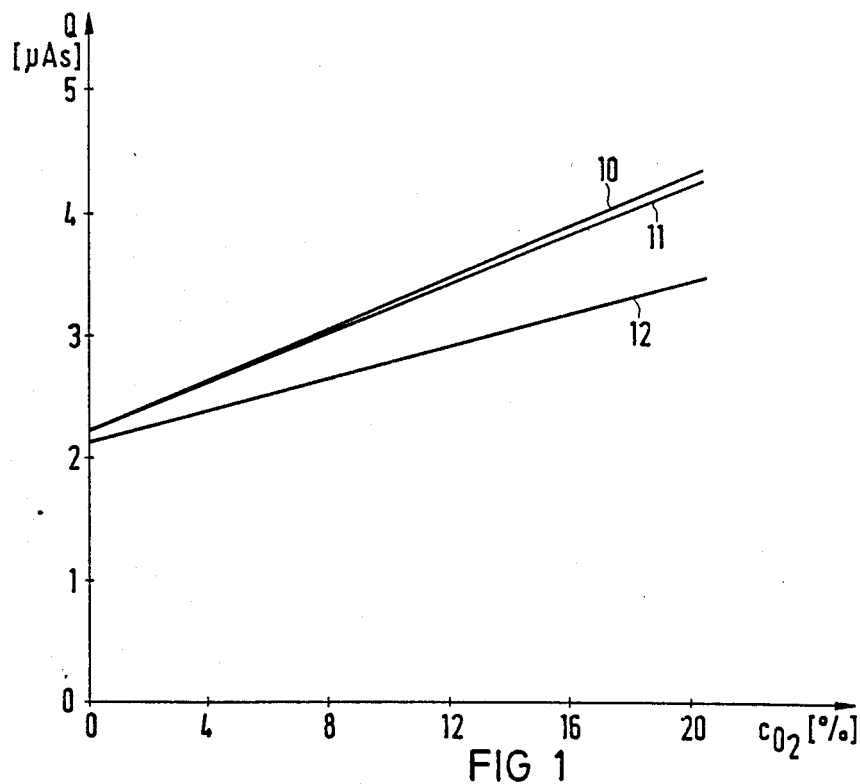
FIGS. 1 and 2 are calibration curves plotting charge Q against oxygen concentrations for the method of the present invention under different conditions.
Figure 2:
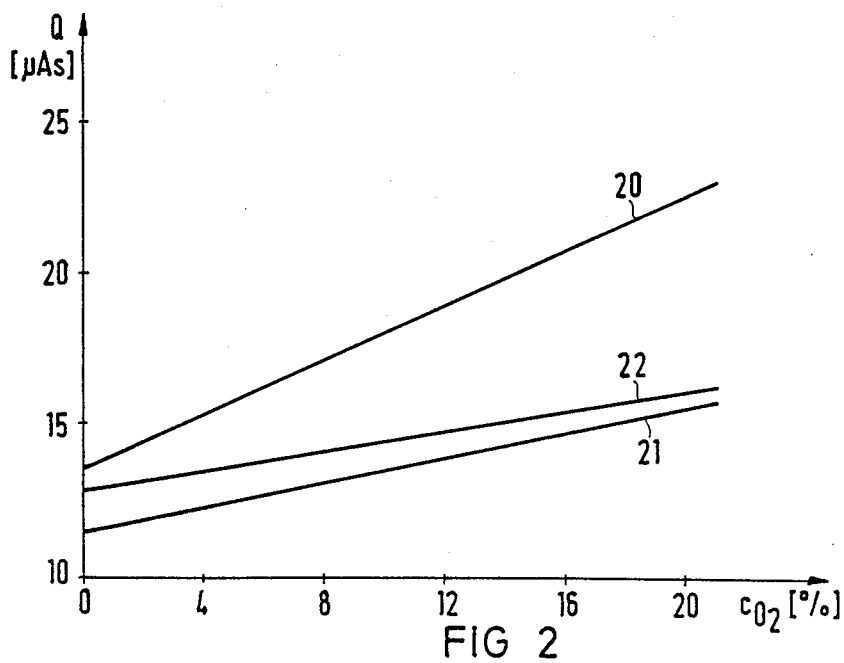

In FIGS. 1 and 2, examples for calibration curves under different conditions are shown (in vitro measurements); the converted charge Q is used as a measure for the oxygen concentration $^cO_2$. The curves 10 (FIG. 1) and 20 (FIG. 2) apply to the base electrolyte; curves 11 and 21 to the base electrolyte with physiological substances; and curves 12 and 22 to cow serum.

In the calibration curves according to FIG. 1, a smooth vitreous carbon electrode was used as the measuring electrode; in the calibration curves according to FIG. 2, a gold electrode was used as the measuring electrode; a platinum electrode was used as the counter electrode and an Ag/AgCl electrode was used as the reference electrode.

The measurements were carried out at room temperature, i.e., at about 24 to 28 C. For both measuring electrodes, the cycle duration was 1 sec and the measuring period, 50 msec. The recovery potential was about 0 V and for both electrodes; the measuring potential with the vitreous carbon electrode was about $-1$ V and in the case of the gold electrode approximately $-0.8$ V each time referred to the Ag/AgCl reference electrode.

It can be seen from FIGS. 1 and 2 that good calibration curves are obtained for the base electrolyte as well as in the presence of physiological substances, i.e., of glucose, urea and amino acids, and also if cow serum is used as the electrolyte.

Figure 4:
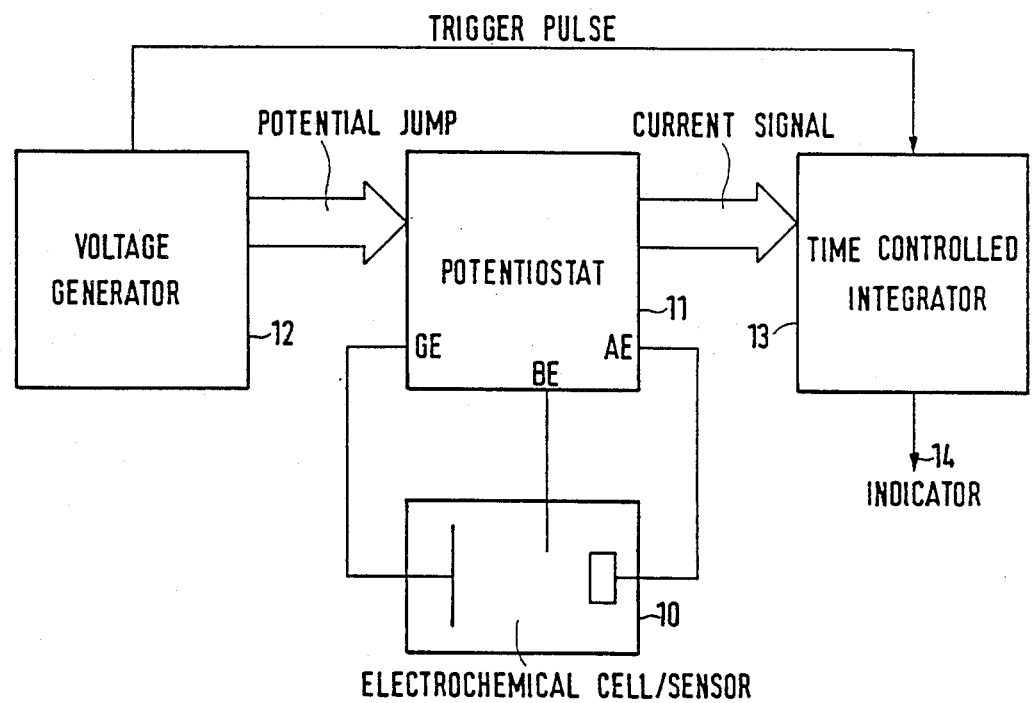
FIG. 4 is a block diagram of apparatus according to the present invention.

FIG. 4 is a block diagram of an oxygen monitor according to the present invention. This oxygen monitor comprises an oxygen sensor 10, i.e., an electrochemical cell, with a measuring electrode AE, a counter electrode GE and a reference electrode BE; a potentiostat 11, a voltage generator 12 and a time controlled integrator 13. The three electrodes of the oxygen sensor 10 are connected to the potentiostat 11. The voltage generator 12 supplies its signal, in the form of a potential jump, to the potentiostat 11, by means of which the course of the cycles with the two potentials is fixed. When the potential jumps to the more negative value, i.e., to measuring potential, the voltage generator 12 delivers a trigger pulse to the time controlled integrator 13. The integrator 13 then begins to integrate the current which flows through the measuring electrode via the potentiostat 11 and which it receives from the potentiostat 11 in the form of a current signal, until, at the end of the measuring period, the potential is changed again. The measuring signal, in the form of the amount of the charge, which in this manner is not influenced by the capacitive current of the recharge of the double layer, or the corresponding value of the oxygen concentration, then reaches the indicator 14.

Figure 5A:
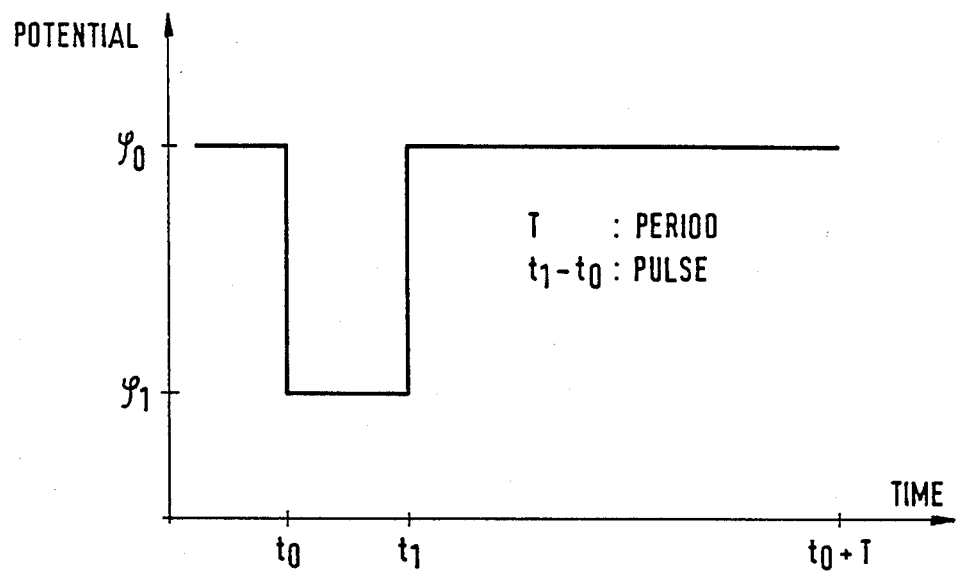
FIGS. 5 and 5b are plots of voltage and current respectively as a function of time.
Figure 5B:
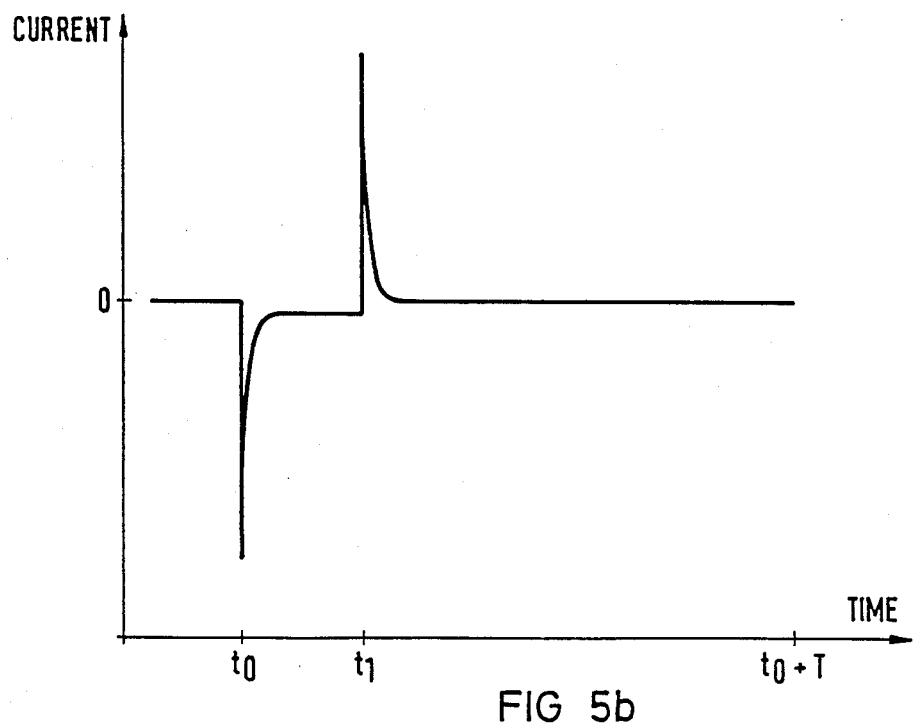

FIG. 5a illustrates the typical potential course with time. The current response of the measuring electrode, that is, the current signal is shown in FIG. 5b. The measuring potential is applied during the time $t_0$ to $t_1$ to the measuring electrode. A current flows which is initially determined by the recharging of the double layer capacity and then changes to a reaction current for the oxygen reduction. The integration of the current takes place preferably during the time interval between the end of the recharging and the time point $t_1$.

The measuring electrode is preferably designed with a hemispherical shape, that is, it has a shape which is usual also for stimulating electrodes; the surface area generally amounts to approximately 0.1 $cm^2$.

Figure 3:
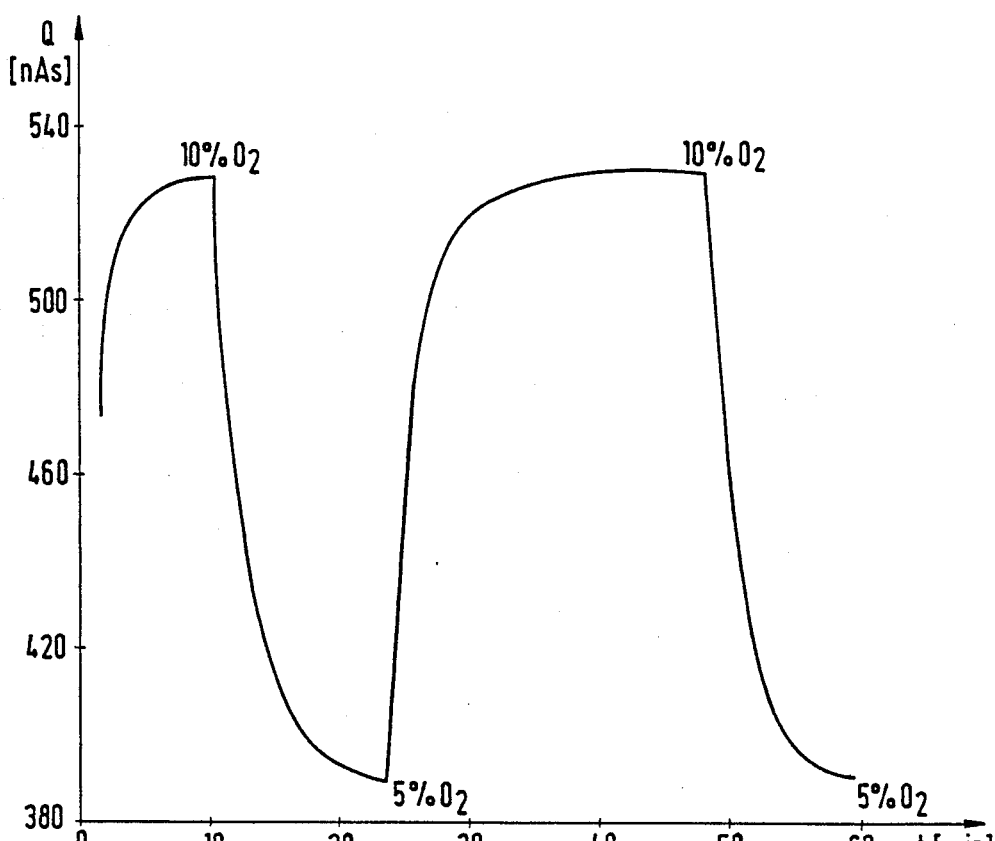
FIG. 3 is a curve showing the Charge Q as a function of time.

With such an oxygen monitor, the oxygen concentration in human serum was determined, the results of which are shown in FIG. 3. The oxygen concentration was changed in steps, a mixture of $0_2$, $C0_2$ and $N_2$ comprised the gas supply. It can bee seen from FIG. 3 that the response time of the oxygen sensor in human serum (a vitreous carbon electrode was used as the measuring electrode) is relatively short in the event of a change of the oxygen concentration.

What is claimed is:

1. A method for the electrochemical determination of oxygen concentration by means of an oxygen sensor with a measuring electrode comprising a smooth vitreous carbon or pyrographite electrode and further having a counter electrode, comprising cyclically impressing two potentials on the measuring electrode, one potential comprising a measuring potential in the range $-1.4\ V \leq pAg/AgCl \leq -0.4\ V$ and another potential comprising a recovery potential in the range $0.2\ V \leq pAg/AgCl \leq +0.2\ V$; maintaining a small dwelling time at the measuring potential with respect to the duration of the cycle; and evaluating a current flowing during the measuring period as the measuring signal; the cycle time of said cycle being between 0.5 and 10 seconds, said dwelling time at the measuring potential being between 5 and 100 msec, said counter electrode comprising a material which is inert and biocompatible and having a high double layer capacity relative to said measuring electrode, a diffusion membrane not being placed betwen said measuring electrode and the material whose oxygen concentration is being measured, said dwelling time at the measuring potential being substantially smaller than said cycle time whereby oxygen loss from the material whose oxygen concentration is being measured is compensated during the time during which the recovery potential is applied.

2. The method according to claim 1, wherein the cycle time is between 1 and 5 seconds.

3. The method according to claim 1 or 2, wherein the dwelling time at the measuring potential is between 10 and 50 msec.

4. The method according to claim 1, wherein the current is evaluated with a time delay relative to the start of the measuring period.

5. The method according to claim 4, wherein the current is evaluated 2 to 40 msec after the start of the measuring period.

6. The method according to claim 4 wherein the current is evaluated 10 to 15 msec after the start of the measuring period.

7. The measuring according to claim 1, wherein the transferred charge is used to determine the measuring signal.

8. The method according to claim 1, wherein said method comprises a method for the electrochemical determination of the oxygen concentration in biological matter.

9. The method according to claim 1, wherein a platinum electrode is used as the counter electrode.

10. The method according to claim 1 and further including using, in addition, a reference electrode.

11. The method according to claim 10 wherein said reference electrode is a Ag/AgCl electrode.

12. Apparatus for the electrochemical determination of oxygen concentration comprising:
  (a) an oxygen sensor having a measuring electrode comprising a smooth vitreous carbon electrode or a pyrographite electrode and a counter electrode comprising a material which is inert and biocompatible and having a high double layer capacity relative to the measuring electrode;
  (b) means for cyclically impressing two potentials on the measuring electrode including a measuring potential in the range $-1.4\ V \leq \pi Ag/AgCl \leq -0.4\ V$ and a recovery potential in the range of $-0.2\ V \leq \pi Ag/AgCl \leq +0.2\ V$, such that a dwelling time at the measuring potential is small with respect to the duration of the cycle;
  (c) means for evaluating the current flowing during at least part of the time the measuring potential is applied to obtain a measurement of a value proportional to oxygen content;
  the cycle time of said cycle being between 0.5 and 10 seconds and the dwelling time at the measuring potential being between 5 and 100 msec, a diffusion membrane not being placed between said measuring electrode and the material whose oxygen concentration is being measured, said dwelling time at the measuring potential being substantially smaller than said cycle time whereby oxygen loss from the material whose oxygen concentration is being measured is compensated during the time during which the recovery potential is applied.

13. Apparatus according to claim 12, wherein a platinum electrode is used as the counter electrode.

14. Apparatus according to claim 12 and further including a reference electrode.

15. Apparatus according to claim 14 wherein said reference electrode is a Ag/AgCl electrode.

* * * * *